US011771579B2

(12) United States Patent
Princip

(10) Patent No.: US 11,771,579 B2
(45) Date of Patent: Oct. 3, 2023

(54) PROTECTIVE SUPPORT FOR JOINTS AND EXTREMITIES

(71) Applicant: Michael Princip, Winston-Salem, NC (US)

(72) Inventor: Michael Princip, Winston-Salem, NC (US)

(*) Notice: Subject to any disclaimer, the term of this patent is extended or adjusted under 35 U.S.C. 154(b) by 525 days.

(21) Appl. No.: 16/930,559

(22) Filed: Jul. 16, 2020

(65) Prior Publication Data

US 2021/0015648 A1   Jan. 21, 2021

Related U.S. Application Data

(60) Provisional application No. 62/936,946, filed on Nov. 18, 2019, provisional application No. 62/876,129, filed on Jul. 19, 2019.

(51) Int. Cl.
*A61F 5/01* (2006.01)
*A41D 13/06* (2006.01)

(52) U.S. Cl.
CPC .......... *A61F 5/0125* (2013.01); *A41D 13/065* (2013.01); *A61F 2005/0137* (2013.01); *A61F 2005/0179* (2013.01)

(58) Field of Classification Search
CPC ........ A61F 5/0125; A61F 5/01; A61F 5/0102; A61F 5/0104; A61F 5/0106; A61F 5/0118; A61F 5/0123; A61F 5/0127; A61F 5/013; A61F 2005/0137; A61F 2005/0179; A61F 2005/0174; A61F 2005/0176; A61F 5/0109; A61F 5/0111; A61F 2005/0197; A41D 13/065; A41D 13/0575; A41D 13/0581; A41D 13/0587; A41D 13/0593; A41D 13/05; A41D 13/055; A41D 13/0556; A41D 13/06; A63B 21/4025; A63B 21/065; A63B 21/4023; A43C 11/14; A43C 11/22; F16G 11/046; Y10T 16/525; Y10T 16/5257; E05D 1/00; E05D 1/02; E05D 9/005
USPC .......................................................... 602/26
See application file for complete search history.

(56) References Cited

U.S. PATENT DOCUMENTS

| 4,941,465 A * | 7/1990 | Borschneck .......... A61F 5/0585 |
| | | 128/99.1 |
| 2015/0173926 A1* | 6/2015 | Bichler ................ A61F 5/0111 |
| | | 602/12 |
| 2019/0048923 A1* | 2/2019 | Gunnsteinsson ......... E05D 1/02 |

* cited by examiner

*Primary Examiner* — Alireza Nia
*Assistant Examiner* — Daniel A Miller
(74) *Attorney, Agent, or Firm* — Matthew L. Jamison

(57) ABSTRACT

The invention disclosed herein is a protective support for joints and extremities comprising a structure for securing the support to the body in the vicinity of the joint, one or more elongated resilient hinges that are attached to the support. Each resilient hinge spans a parasagittal plane of the joint and has a superior end, an opposite inferior end, and an intermediate section there between, the hinge also defining a cross-sectional thickness that is at its minimum near the superior end and inferior end, but gradually increases along a length of the hinge such that the intermediate section defines the hinge's maximum cross-sectional thickness. Each hinge may define a plurality of longitudinal ribs and optional transverse ribs that aid in structural integrity of the hinge and may have a generally hourglass shape, and with the superior and inferior ends adapted to conform to the various superficial contours of the joint or extremity.

20 Claims, 19 Drawing Sheets

PROTECTIVE SUPPORT FOR JOINTS AND EXTREMITIES

CROSS REFERENCE TO RELATED APPLICATIONS

This application claims priority to U.S. Provisional Patent Application No. 53/3,115,672, filed Jul. 26, 2019, and U.S. Provisional Patent Application No. 53/4,517,294, filed Nov. 18, 2019. Each of the patent applications, listed above are expressly incorporated by reference herein.

BACKGROUND OF THE INVENTION

The human body's joints, tendons, ligaments, and muscles are susceptible to all manner of injury, fatigue, and instability. Such afflictions may be the result of numerous causes, including degenerative wear, athletic injury, over exertion, or the aging process. The pain and instability associated with joint injury can be particularly acute when localized in the body's hinge joints, such as the knee, elbow, or other joints that allow for angular movement between bones. External devices, in the form of a splint or brace, are often worn to improve stability, reduce or restrict motion, or to protect the joint from further injury. Athletes frequently wear such supports as a preventative measure to reduce the risk of injury.

Additionally, many sports also present the risk of collision, impact, or sliding contact that can result in superficial damage to the epidermis at the medial and lateral areas of the hinge joints. For example, in sports played on artificial playing surfaces, it may be desirable to wear a lightweight device that protects the epidermis from abrasion injuries, so long as the device does not impede movement or adversely impact the athlete's performance. Such devices can reinforce standard worn athletic apparel such as padded compression shirts, pants, and leather protective apparel to provide extra protection from both injures to the joints and/or to the epidermis.

SUMMARY OF THE INVENTION

The invention disclosed herein is a protective support for joints and extremities suited to reduce the risk and impact of injury to such joints. In particular, the present invention is, in a preferred embodiment, a protective support for spanning a hinge joint in a body that provides, among other things, a structure for securing the support to the body in the vicinity of the joint, one or more elongated resilient hinges that are attached to the support such that each hinges is located adjacent to a parasagittal plane of the joint and providing a plurality of longitudinal ribs and optional transverse ribs that aid in structural integrity of the hinge.

The invention, in another preferred embodiment relates to a resilient hinge for providing protective support to a hinge joint in a body by spanning a parasagittal plane of the joint, where the said hinge has a superior end, an opposite inferior end, and an intermediate section there between, where the hinge has a cross-sectional thickness that is at its minimum near the superior end and inferior end, but gradually increases along a length of the hinge such that the intermediate section defines the hinge's maximum cross-sectional thickness. This tapering cross-sectional thickness provides support for the body's hinge joint by preventing excessive flexion or torsion of the joint. Additionally, the hinge may have a generally hourglass shape, and with the superior and inferior ends adapted to conform to the various superficial contours presented by a hinge joint.

Additional aspects of example embodiments will be set forth in part in the provided figures and description below, in part, will be apparent from the figures and/or description, or may be learned through practicing this invention.

BRIEF DESCRIPTION OF THE DRAWINGS

Several embodiments of the invention will now be described in detail with reference to the accompanying drawings, wherein similar elements are referred to with similar reference numerals.

DETAILED DESCRIPTION

The singular terms "a," "an," and "the" include plural referents unless context clearly indicates otherwise. The term "comprises" means "includes." In case of conflict, the present specification, including explanations of any terms, will control.

Figure 1:
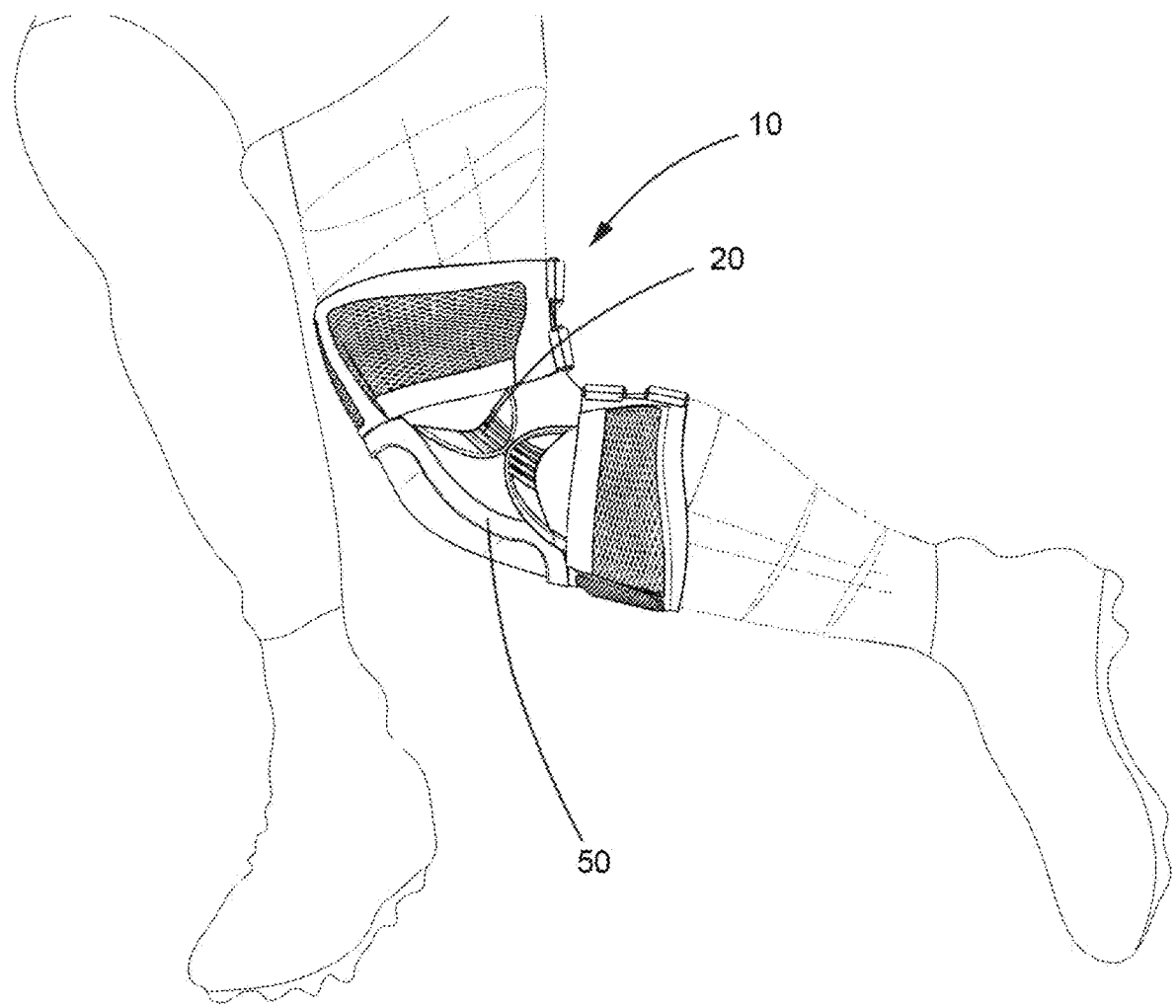
FIG. 1 is a perspective view of a protective support of the present invention, shown from the lateral side of an individual's right knee.

Referring now to the drawings a first a preferred embodiment of the protective support, generally identified by reference numeral 10, is shown in FIG. 1. Support 10 has at least one hinge 20 and at least one support structure 50 for attaching hinge 20 to the joint or appendage of the wearer. FIG. 1 shows protective device 10 worn by an individual on the right knee with structure 50 providing secure contact to the portions of the individual's leg that are superior to the knee (i.e., the thigh) and inferior to the knee (i.e., the calf) and hinge 20 disposed along a parasagittal plane defined by the knee, in this instance the medial side of the knee. It should be understood that the present invention can also be used for other joints, such as elbows, shoulders, hips, and the like, and that hinge 20 may be disposed on either or both parasagittal plane(s) of the joint (i.e. lateral side and/or medial side).

Figure 2:
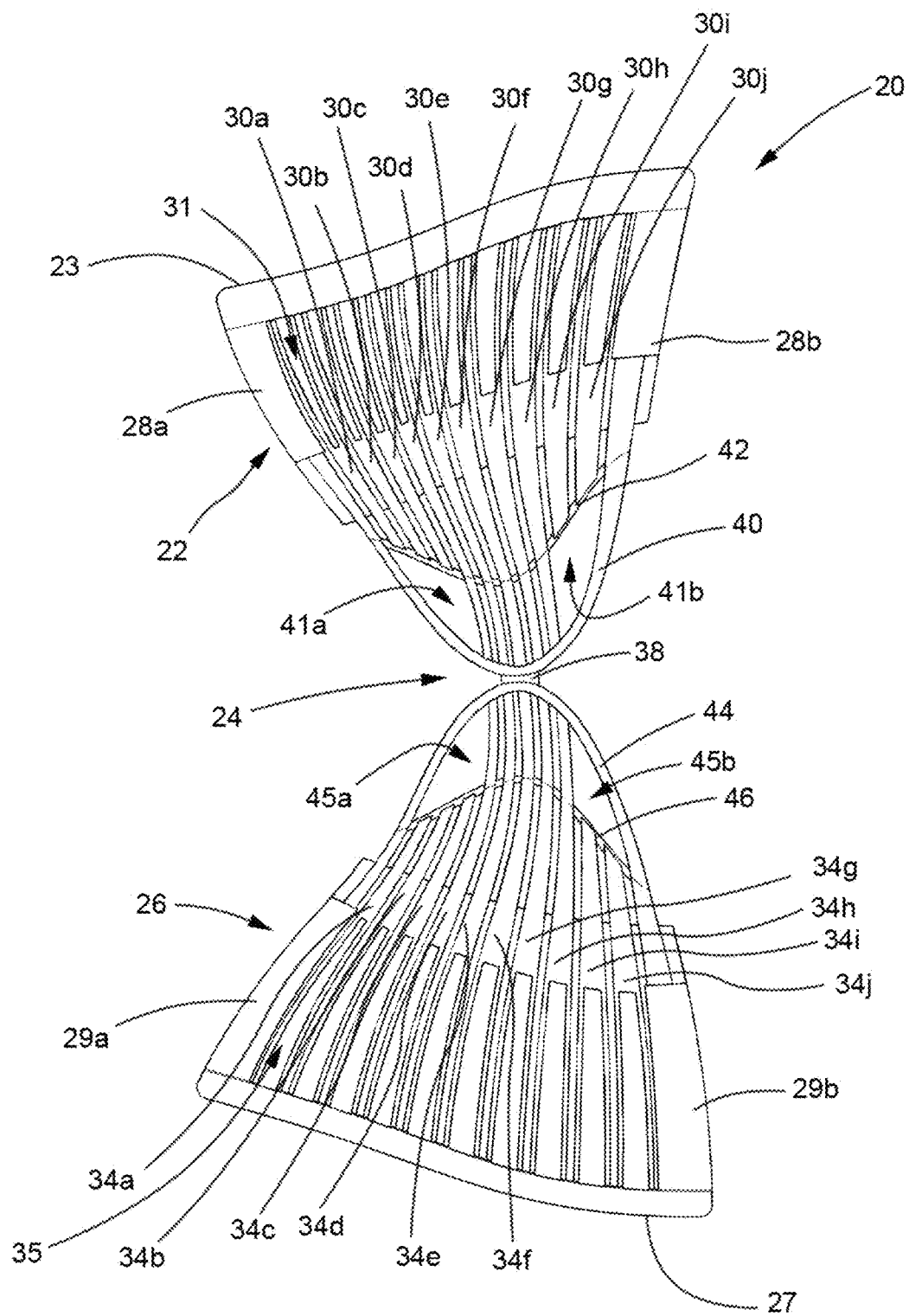
FIG. 2 is a top view of a preferred embodiment of a hinge element of the present invention.

With reference to FIG. 2, Hinge 20 is preferably elongated with a length that is greater than its maximum width and includes an upper or superior section 22, a lower or inferior section 26, and an intermediate section 24 therebetween. Sections 22 and 26 preferably taper from their broadest width distal from intermediate section 24 to their most narrow width proximate thereto, thus giving the hinge a generally hourglass shape when viewed from the top or bottom. This preferred shape of Sections 22 and 26, along with their respective optional retention wings 28a-b and 29a-b facilitate secure attachment of hinge 20 to structure 50 (FIG. 1), as described in greater detail below.

Figure 5A:
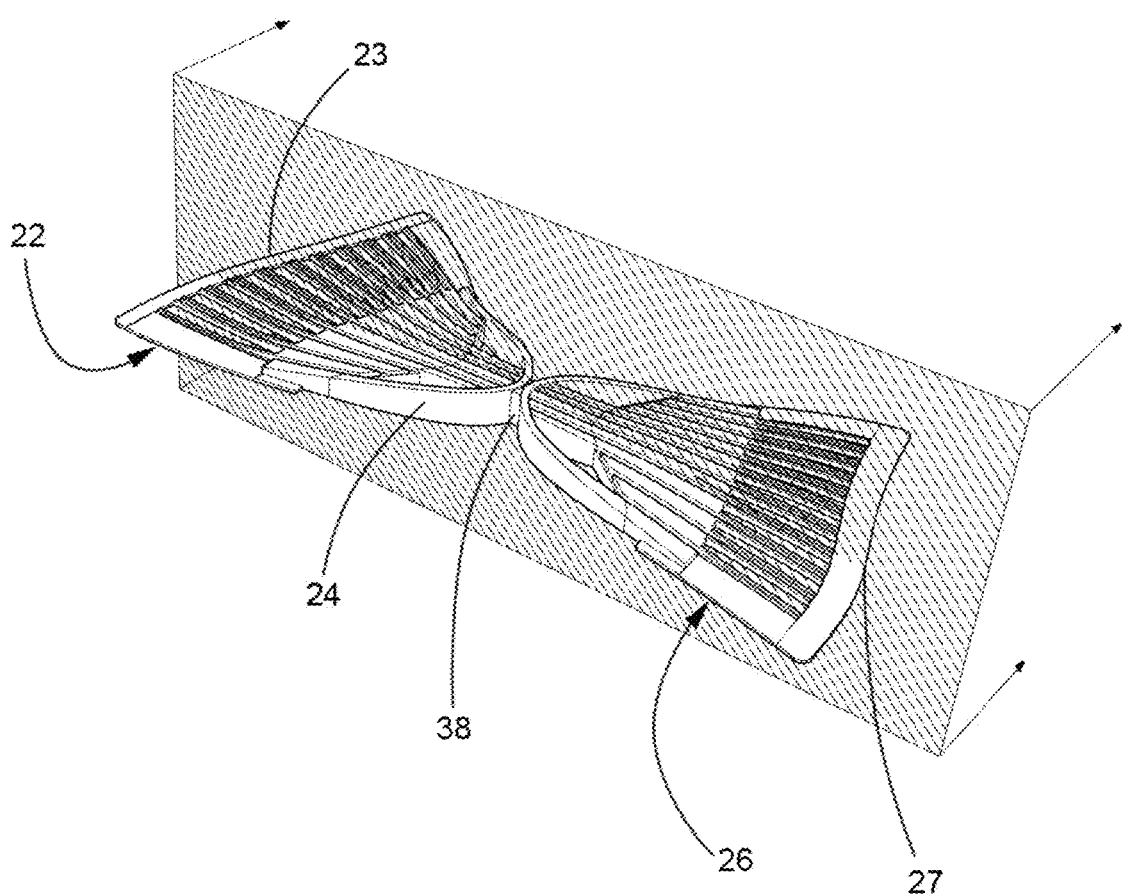
FIG. 5a is a top perspective view of a hinge element of the present invention.
Figure 5B:
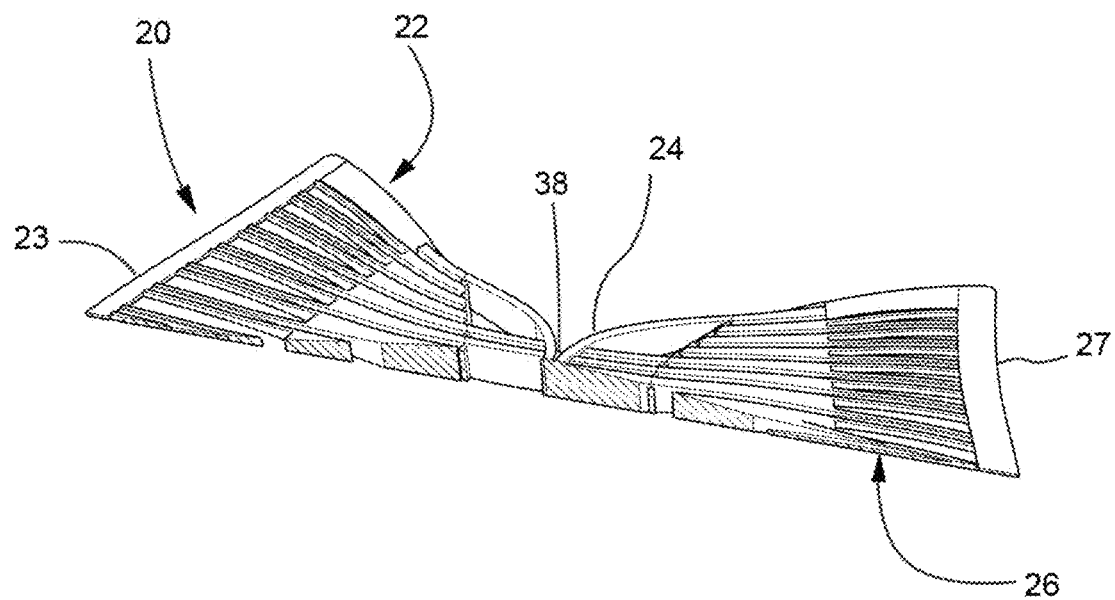
FIG. 5b is a section view of the hinge shown in FIG. 5 shown from a top perspective.

Superior section 22 preferably defines a plurality of longitudinal ribs 30a-j that run generally along the longitudinal length thereof from distal edge 23 of section 22 to their termination at a major transverse rib 40. Similarly, inferior section 24 also defines a plurality of longitudinal ribs 34a-j that run generally along the longitudinal length thereof from distal edge 27 of section 26 to their termination at a major transverse rib 44. Ribs 30a-j and 34a-j preferably have a tapered profile such that the ribs are quite thin at the distal edges 23, 27, but generally increase in thickness along their length until reaching their maximum thickness in the vicinity of intermediate section 24, most clearly visible in FIGS. 5a, and 5b. Additionally, ribs 30a-j, 34a-j may each define an optional aperture, shown by way of example as 31 on rib 30a and 35 on rib 34a, which facilitate ventilation and moisture management, and reduce the weight of hinge 20.

In a preferred embodiment shown in FIG. 2, each section 22 and 26 defines eleven longitudinal ribs; however, it should be apparent that any desirable or appropriate number of ribs may be used as contemplated by this invention. Additionally, in a preferred embodiment, superior section 22 may define a major transverse rib 40 and a minor transverse rib 42. Preferably, transverse ribs 40, 42 define a parabolic or partial sinusoidal curve, but it should be appreciated that other appropriate structural shapes may be substituted. In this arrangement, superior longitudinal ribs 30a-c and 30i-j may terminate at minor transverse rib 42 while ribs 30d-h intersect transverse rib 42 and continue running longitudinally along section 22 until intersecting and terminating at major transverse rib 40. Similarly, inferior section 26 may define a major transverse rib 44 and a minor transverse rib 46, that preferably define a parabolic or partial sinusoidal curve. In this arrangement inferior longitudinal ribs 34a-c and 34i-j may terminate at minor transverse rib 46 while ribs 34d-h intersect transverse rib 46 and continue running longitudinally along section 26 until intersecting and terminating at major transverse rib 44 In this embodiment, the structures of superior section 22, namely major transverse rib 40 together with minor transverse rib 42 and longitudinal rib 30d, define an adjustment recess 41a, while major transverse rib 40 together with minor transverse rib 42 and longitudinal rib 30h define an adjustment recess 41b. Similarly, major transverse rib 44 together with minor transverse rib 46 and longitudinal ribs 34d, 34h define an adjustment recesses 45a and 45b within inferior section 26. However, in alternate embodiments, the superior and inferior sections' longitudinal ribs 30a-c, 30i-j and 34a-c, 34i-j may not terminate at the minor transverse ribs, and, instead extend all the way to their respective major transverse ribs 40, 44. In such alternate embodiments, recesses 41a, 41b, 45a, 45b would be omitted.

Figure 3:
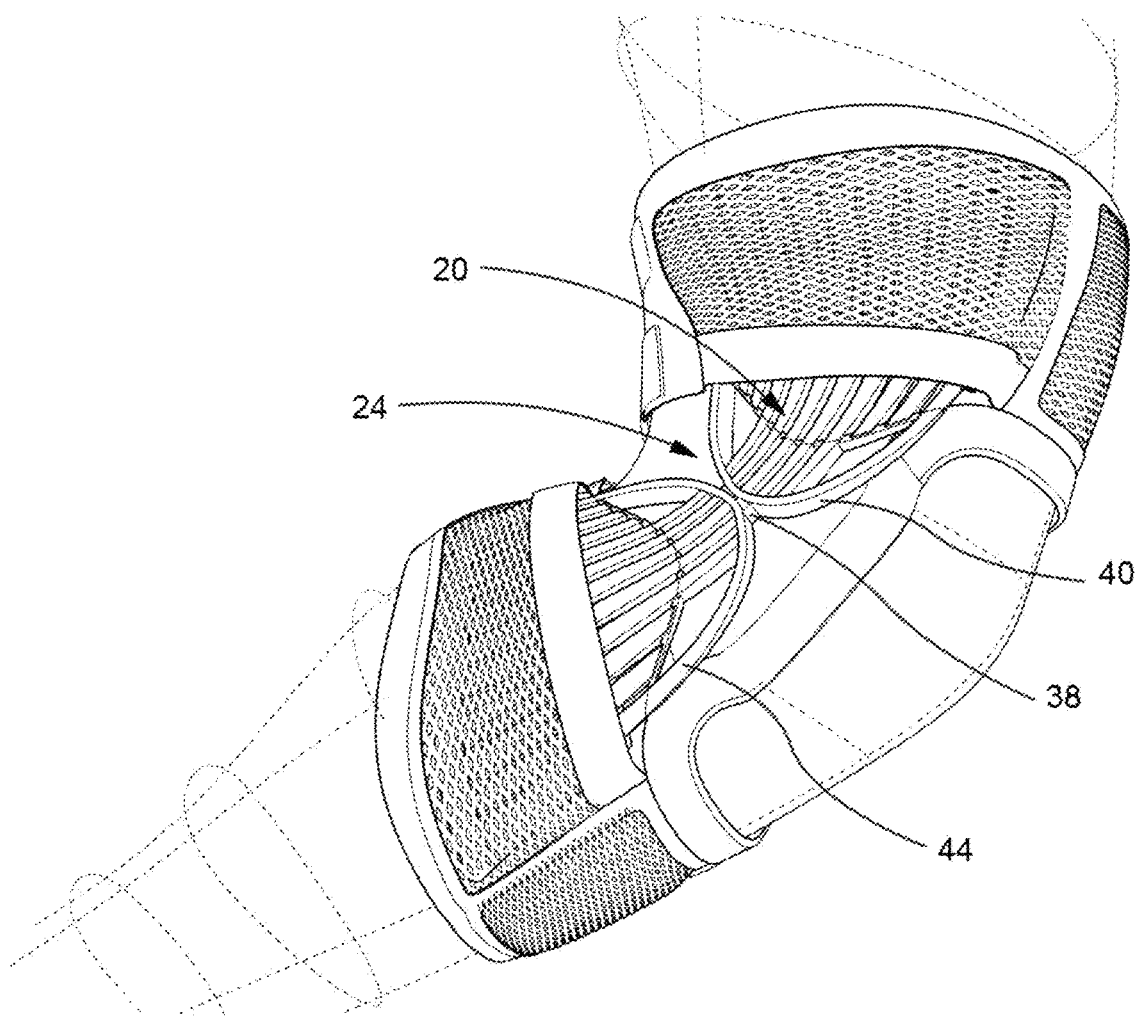
FIG. 3 is a perspective view of the protective support present invention shown from the lateral side of an individual's right knee.
Figure 6:
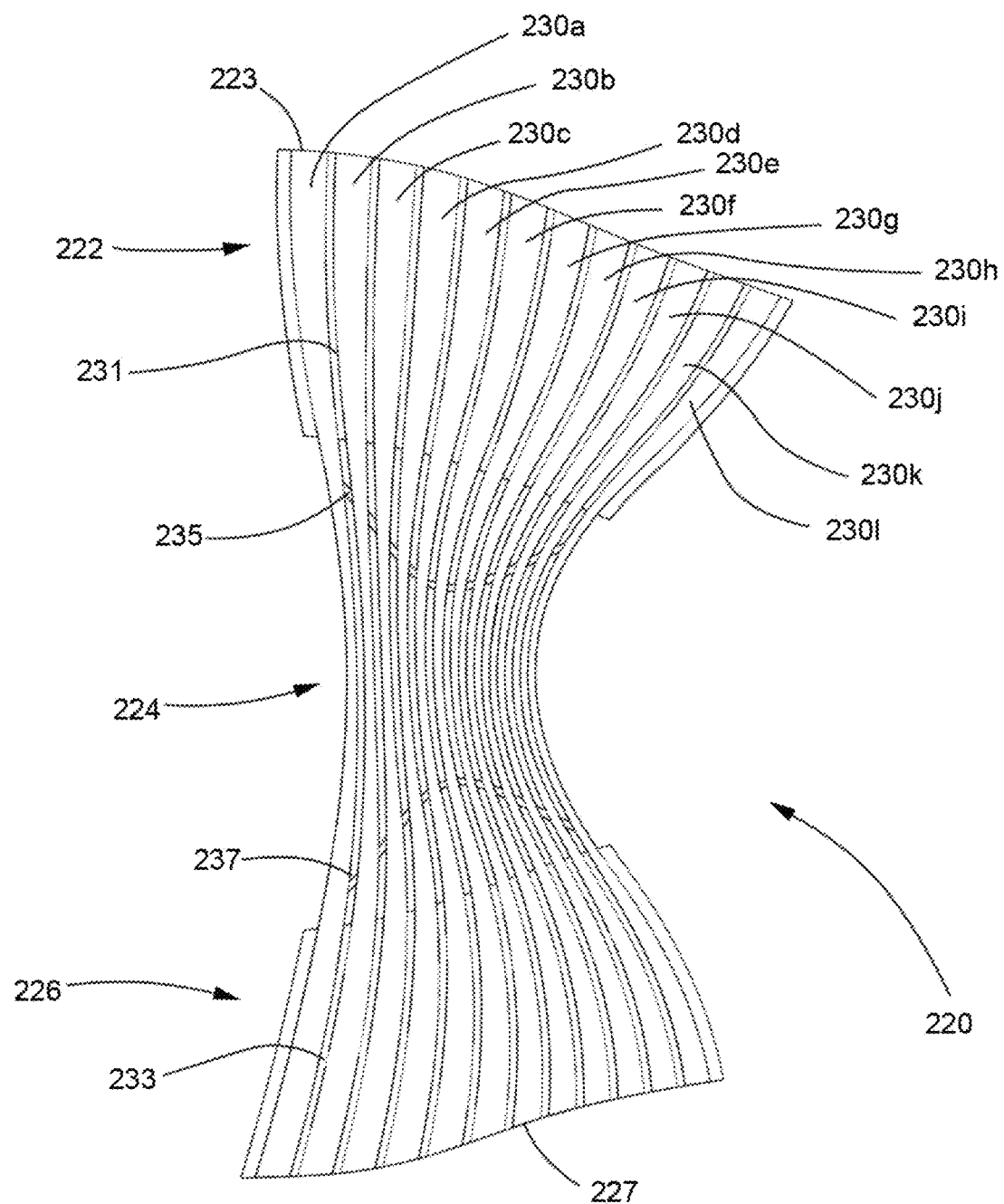
FIG. 6 is a top view of a second, alternate embodiment of a hinge element of the present invention.

In the preferred embodiment shown in FIGS. 2 and 3 intermediate section 24 defines a single intermediate rib 38 that links and provides support between major transverse ribs 40, 44. Furthermore, in other embodiments, some or all of the longitudinal ribs of the superior and inferior sections may traverse the transverse ribs and continue running, uninterrupted, the entire length of the hinge 20, thereby crossing the hinge's major and/or minor transverse ribs, if present. For example, FIG. 6 shows an alternate embodiment of a hinge 220. In this embodiment, longitudinal ribs 230a-l extend the entire length of the hinge from the distal edge 223 of superior section 222 through intermediate section 224 to distal edge 227 of inferior section 226. Webbing, identified, for example, by 231, 233, may be disposed between adjacent ribs (for example, ribs 230a and 230b) in the superior and inferior sections 222 and 224, respectively. Additional webbing, identified, for example by, 235, 237, may also be disposed between adjacent longitudinal ribs (for example, ribs 230a and 230b) proximate to the intermediate section 224 to form transverse ribs that define a generally parabolic or partial sinusoidal shape, thus providing spacing between adjacent ribs and adding overall structural integrity to hinge 220. It should be appreciated that the transverse ribs formed by webbing 235, 237 may be substituted with alternative structures that are equally well suited to space the ribs and provide the hinge with additional structural integrity.

Figure 7:
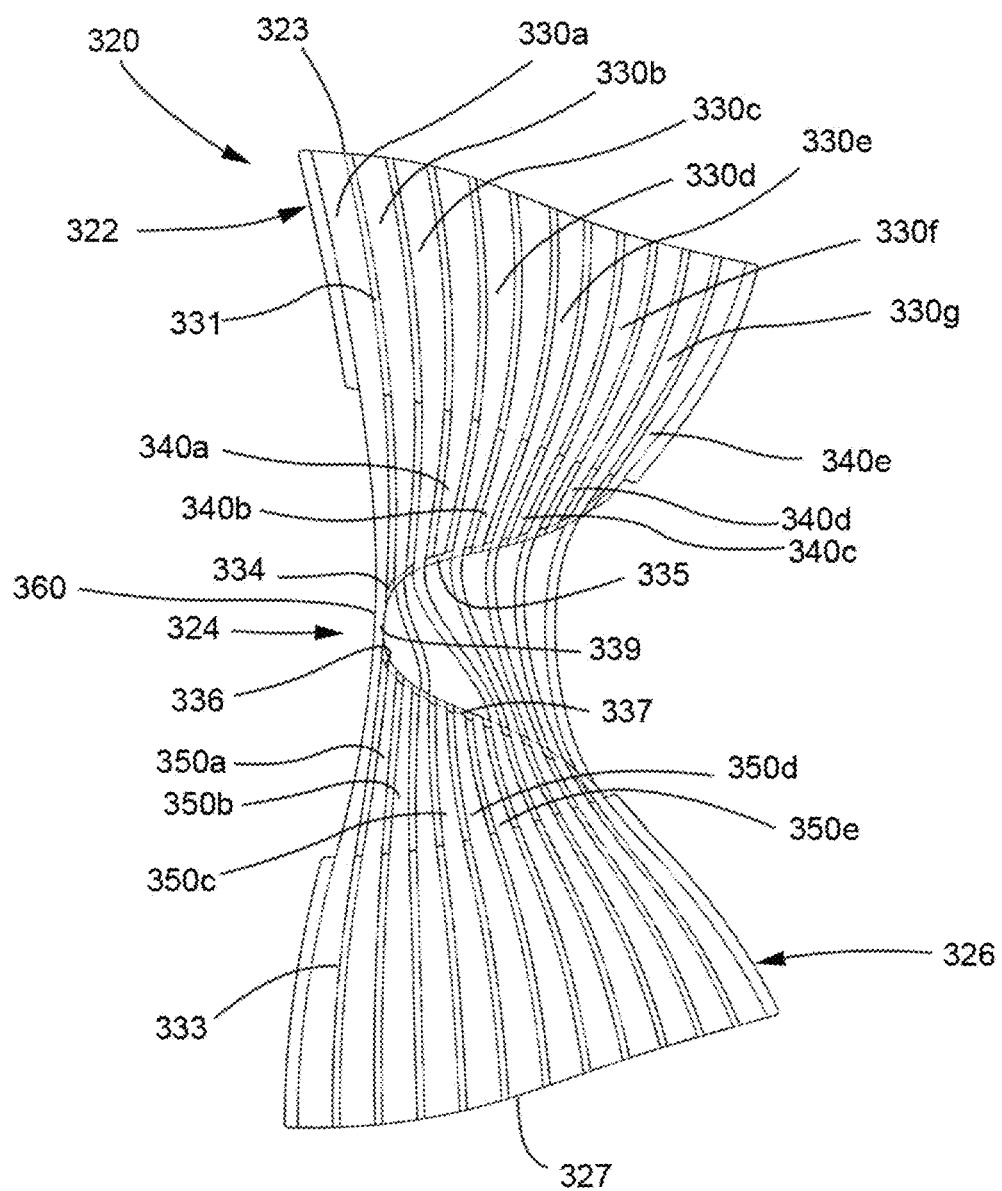
FIG. 7 is a is a top view of a third, alternate embodiment of a hinge element of the present invention.

FIG. 7 shows another alternate embodiment of a hinge 320. In this embodiment, longitudinal ribs 330a-g extend the entire length of the hinge from the distal edge 323 of superior section 322 through intermediate section 324 to distal edge 327 of inferior section 326. Superior section 322 may also define a plurality of superior ribs 340a-e disposed adjacent to and/or between longitudinal ribs, but the superior ribs do not extend the entire length of hinge 320. Similarly, inferior section 326 may also define a plurality of inferior ribs 350a-e disposed adjacent to and/or between longitudinal ribs, but the inferior ribs do not extend the entire length of hinge 320. A plurality of major webbing sections, identified, for example, by 331, may be disposed between adjacent ribs (330a and 330b for example) in superior section 322; likewise a plurality of major webbing sections, identified, for example, by 333, by be disposed between adjacent ribs (330a and 350a for example) in inferior section 324. A plurality of minor webbing sections, identified, for example, by 334 may be disposed between adjacent ribs (for example, ribs 330a and 330b) in superior section 322; likewise a plurality of minor webbing sections, identified, for example, by 336 may be disposed between adjacent ribs (for example 330a and 350a) in inferior section 326. Minor webbing sections 324, 326 may cooperate to define transverse ribs 335, 337 that together define a generally parabolic or partial sinusoidal shape, thus adding structural integrity to hinge 320. It should be appreciated that the transverse ribs formed by webbing 335, 337 may be substituted with alternative structures that are equally well suited to space the ribs and provide the hinge with additional structural integrity. In this embodiment, transverse ribs 335, 337 are positioned such that the vertex 339 of the parabolic shape created thereby is coextensive with rib 330a and located along edge 360, while rib 330g spans across the distance between transverse ribs 335, 337. Furthermore, the portions of longitudinal ribs 330a-g between transverse ribs 335, 337 have a curvilinear shape adapted to flex in response to the flexion of a hinge joint, such as a knee or elbow, when hinge 320 is worn by an individual.

Figure 8:
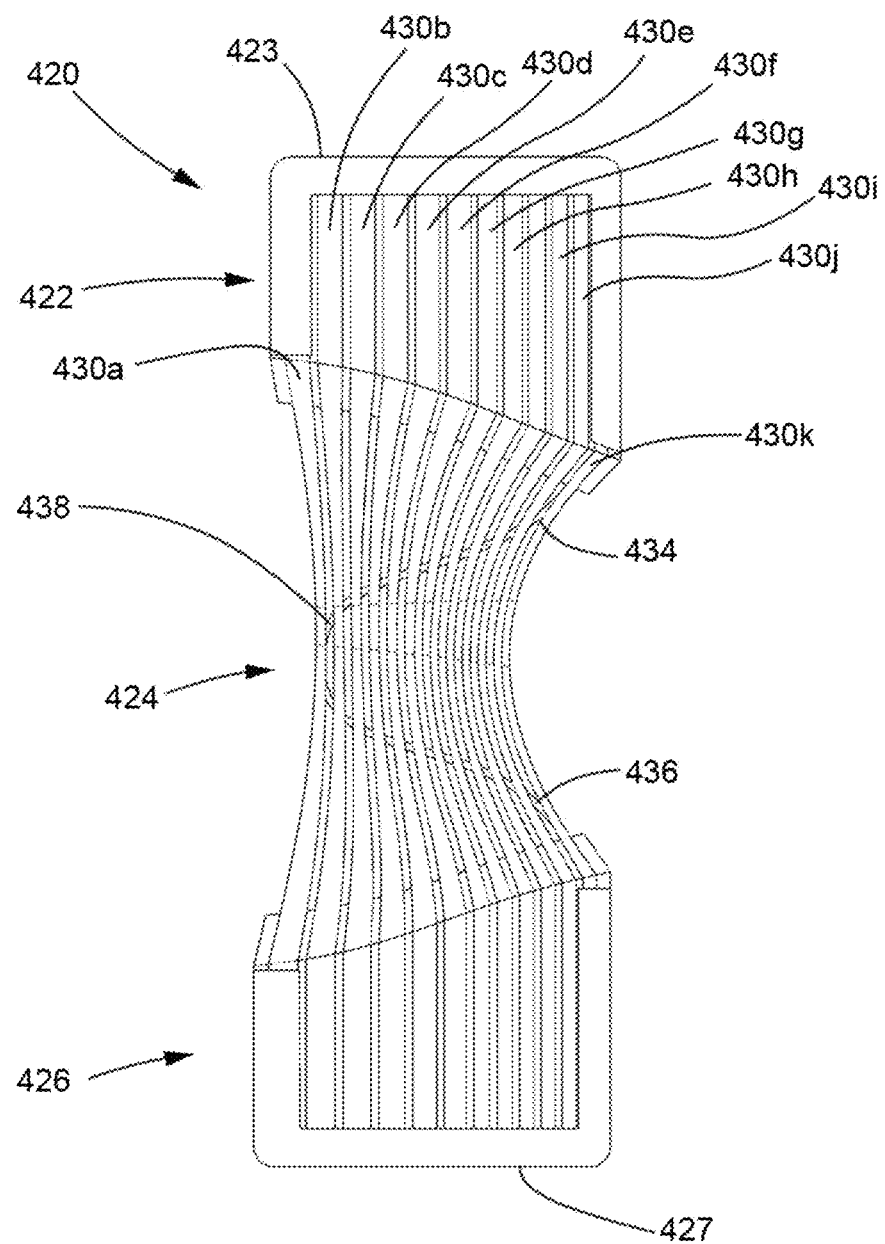
FIG. 8 is a is a top view of a fourth, alternate embodiment of a hinge element of the present invention.

FIG. 8 shows another alternate embodiment of a hinge, 420. In this embodiment, longitudinal ribs 430a-j extend the entire length of the hinge from the distal end 423 of superior section 422 through intermediate section 424 towards distal end 427 of inferior section 426. Webbing sections 434, 436 may be disposed between adjacent longitudinal ribs (for example 430a and 430b), proximate to the intermediate section 424. Webbing sections 434, 436 provide spacing between adjacent ribs and adding overall structural integrity to hinge and, notably, together define a transverse rib 438 that transverses longitudinal ribs 430a-k along a generally parabolic or partially sinusoidal arc that has a vertex that is coextensive with rib 430a. In this embodiment, longitudinal ribs 430a-k preferably exhibit a progressively curvilinear shape adapted to flex in response to the flexion of a hinge joint, such as a knee or elbow. Additionally, in this embodiment, the hinge's preferred hourglass shape is modified such that the superior section 422 and inferior section 426 define a generally square-shaped or trapezium-shape lobes, as opposed to the more generally curvilinear-triangular shape lobes shown in prior embodiments. It should be appreciated that superior and inferior sections of each embodiment disclosed herein may be shaped in any appropriate manner, whether curvilinear-triangular, trapezium, pentagonal, quatrefoil or other shape suitable to attachment to structure 50 and alternative embodiments thereof as described in further detail below.

Figure 9:
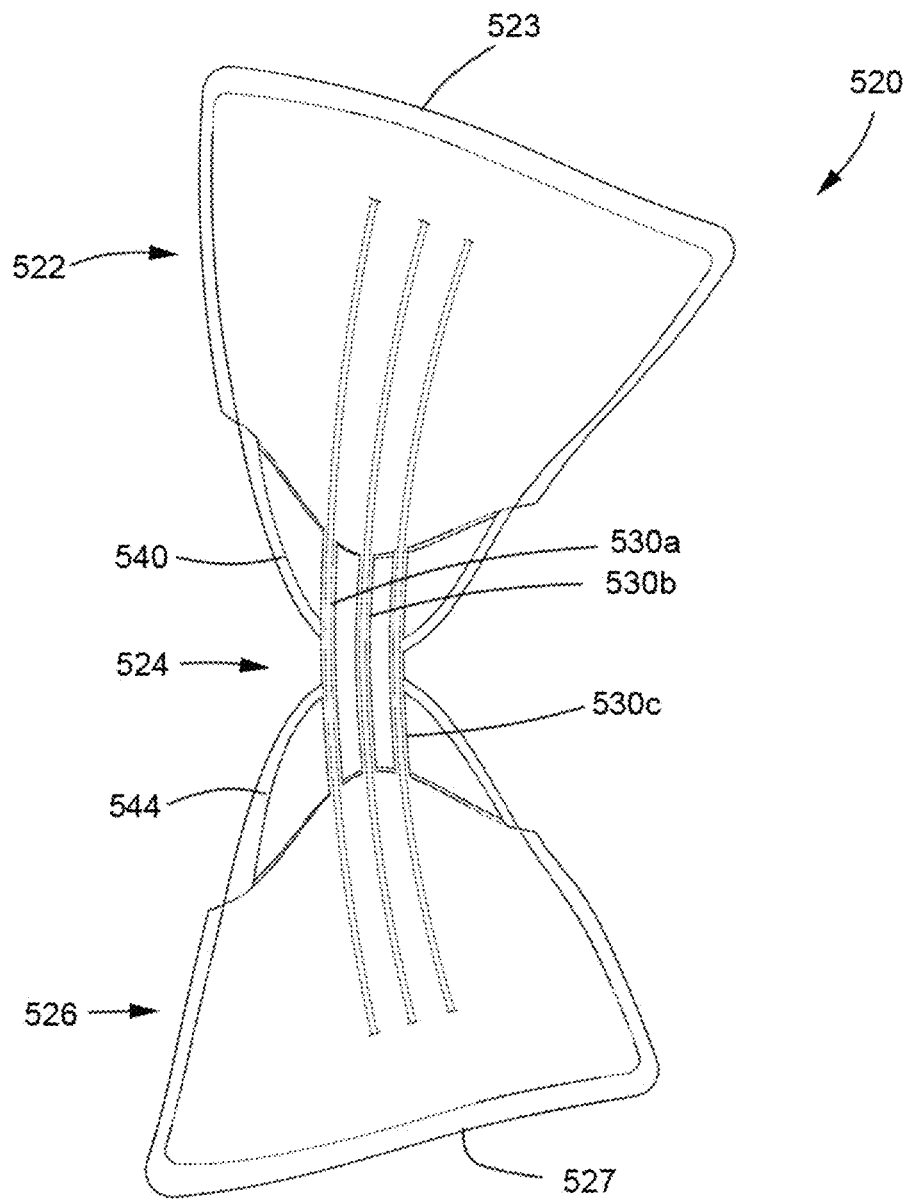
FIG. 9 is a is a top view of a fifth, alternate embodiment of a hinge element of the present invention.
Figure 10:
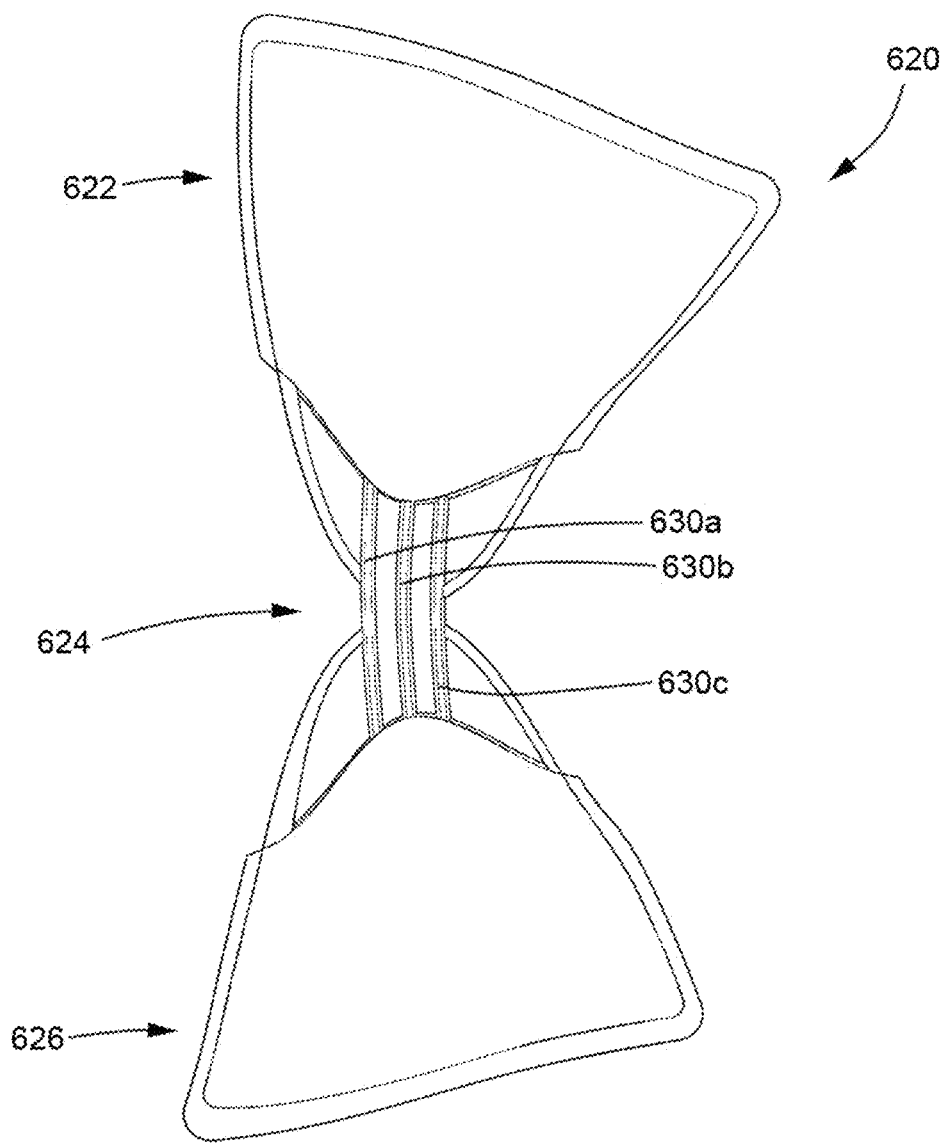
FIG. 10 is a is a top view of a sixth, alternate embodiment of a hinge element of the present invention.
Figure 11:
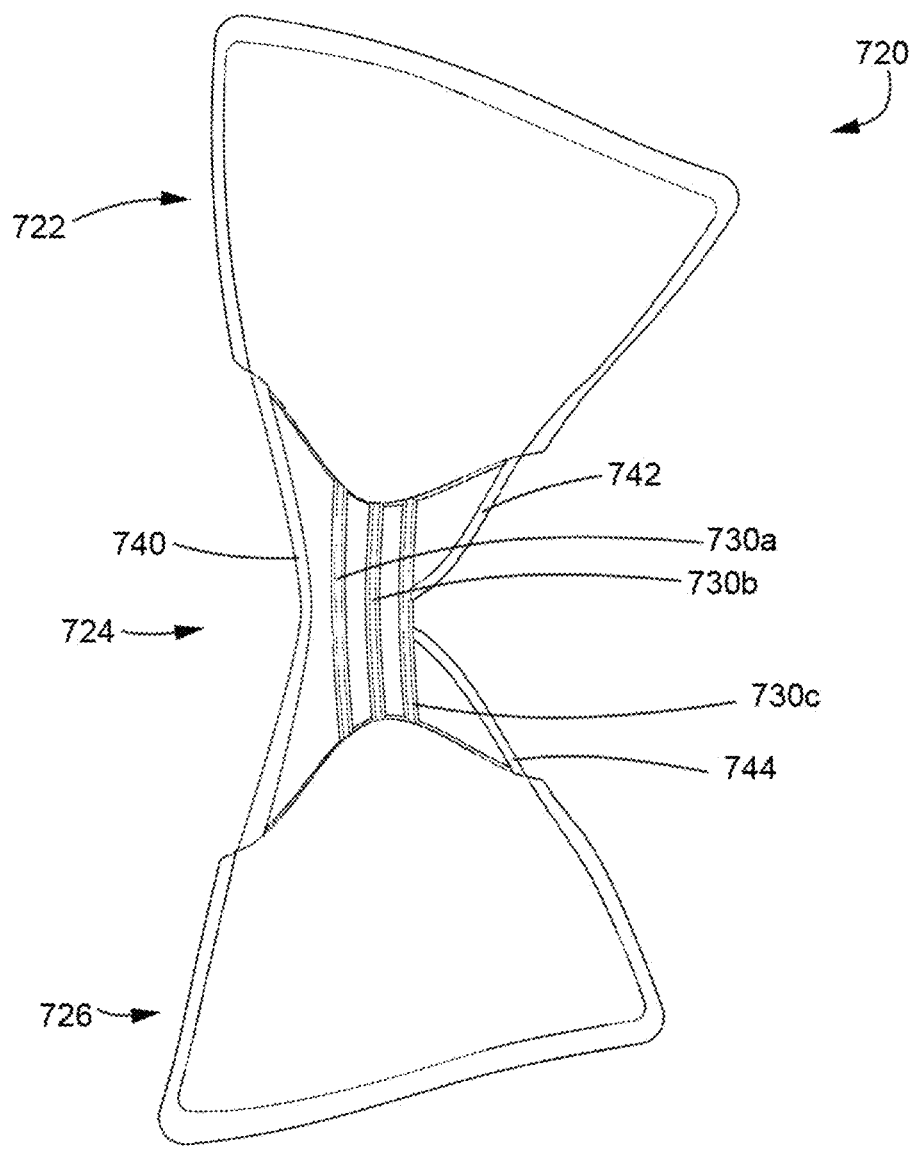
FIG. 11 is a is a top view of a seventh, alternate embodiment of a hinge element of the present invention.

Referring to FIGS. 9-11, three related variants of an additional alternative embodiment a hinge of the present invention. These variants of the hinge may have an hourglass shape similar to embodiments previously described and may define a plurality of longitudinal ribs that do not extend the entire length of the hinge. For example, FIG. 9 shows an embodiment of hinge 520 that defines a plurality of longitudinal ribs 530a-c that emerge from superior section 522 and extend through intermediate section 524 into inferior section 526. Unlike prior embodiments described herein, ribs 530a-c do not extend entirely to distal ends 523, 527. Hinge 520 may also define a superior transverse rib 540 and an inferior transverse rib 544 that follow a parabolic or partial sinusoidal curve that may be bisected by ribs 530a-c.

Similarly, FIG. 10 shows an embodiment of hinge 620 that defines a plurality of longitudinal ribs 630a-c that provide structural integrity to intermediate section 624; however, unlike prior embodiments described herein, ribs 630a-c do not extend into superior section 622 or into inferior section 626. Finally, the hinge variant 720 shown in FIG. 11 defines a plurality of longitudinal ribs 730a-c that emerge extend through intermediate section 724, but do not extend further into superior section 722 or into inferior section 726. Additionally, hinge 720 omits the transverse ribs of prior embodiments, and, instead, defines an anterior edge 740 and two posterior edges 742, 744 that extend from superior section 722 and inferior section 726, respectively, towards intermediate section 724 where they terminate at rib 730c. The embodiments shown in FIGS. 9-11 demonstrate that the longitudinal and transverse ribs contemplated as part of this invention may take different forms and still fall within the scope of this invention.

Figure 12:
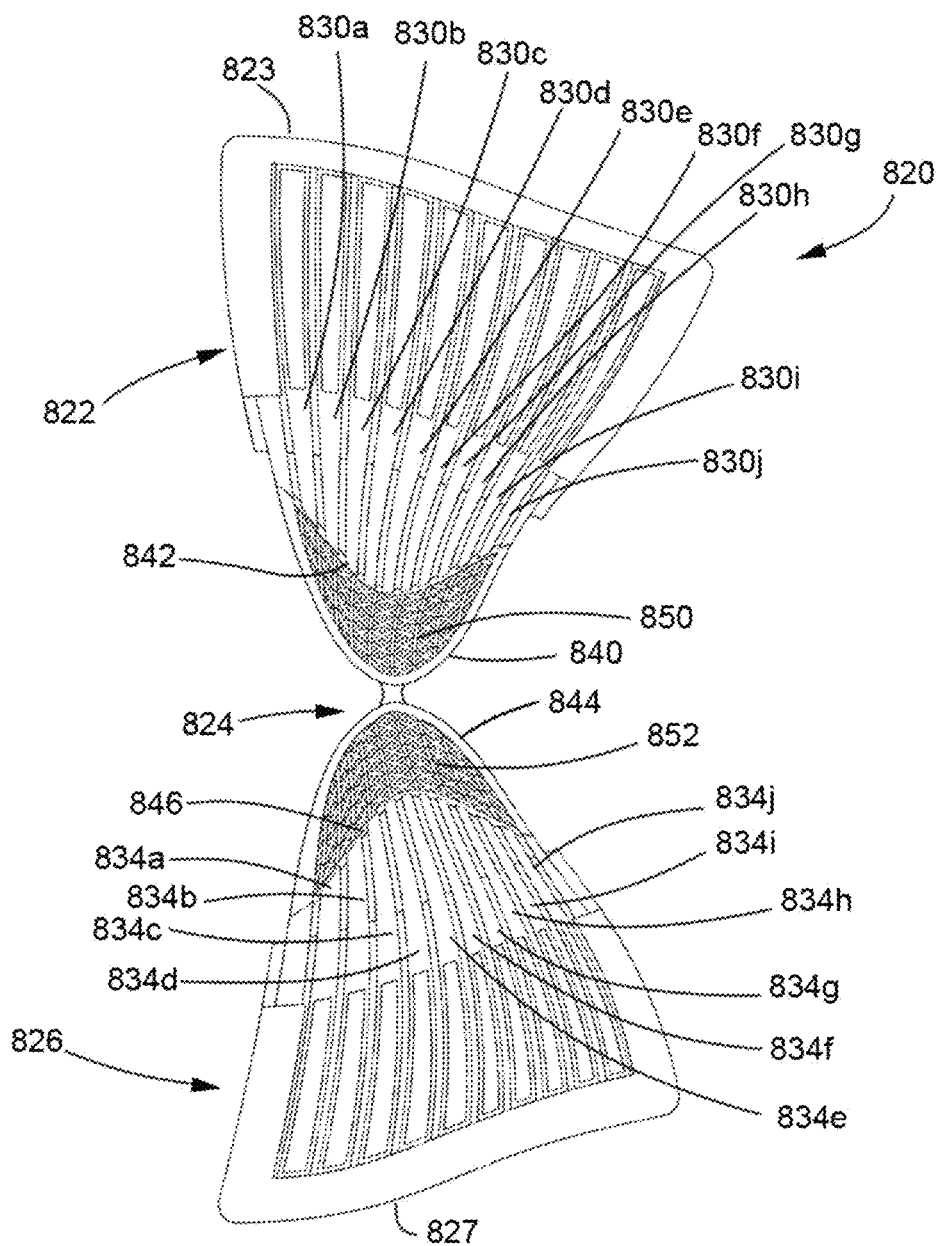
FIG. 12 is a is a top view of an eighth, alternate embodiment of a hinge element of the present invention.

FIG. 12 shows an embodiment of hinge 820, whereby superior section 822 and inferior section 826 each define a plurality of longitudinal ribs 830a-j, and 834a-j, respectively and a major transverse rib 840, 844, respectively. The longitudinal ribs do not extend the entire length of hinge 820, but rather extend from distal ends 823, 827 and terminate proximate to intermediate section 824 at minor transverse rib 842 and minor transverse rib 846 as shown. Additionally, in a preferred embodiment, the areas defined between ribs 840, 842 and 844, 846 each define a lattice structure 850, 852 that may provide the superior and inferior sections structural integrity proximate to intermediate section 824 while reducing the overall weight and material of the hinge. It should be appreciated that any appropriate lattice arrangement may be used, thus allowing for the hinge to be customized to the particular needs of the athlete or individual utilizing the hinge and brace.

Each embodiment of the hinge disclosed herein is preferably formed from a durable but flexible elastomeric materials, such as thermoplastic polyurethane ("TPU"), ethylene vinyl acetate ("EVA"), dilatant material a.k.a. non-Newtonian fluid derived foam, or other similar materials that provide resilience which allows for some range of plastic deformation. Use of such materials, when combined the design of the hinge, provide an additional benefit in allowing the hinge to closely conform to the contours of the joint or extremity on which it is worn. Manufacture of the complex shape and structure of the hinge can be achieved using modern three-dimensional printing technology and materials, however more conventional injection molding and other industrial processes may offer desirable manufacturing and economic advantages. Additionally, the hinge disclosed herein may be co-molded from two or more flexible elastomeric materials, such as TPU, EVA, and other similar materials, in order to combine the various durability and elastomeric properties of the materials into a single hinge.

Figure 13:
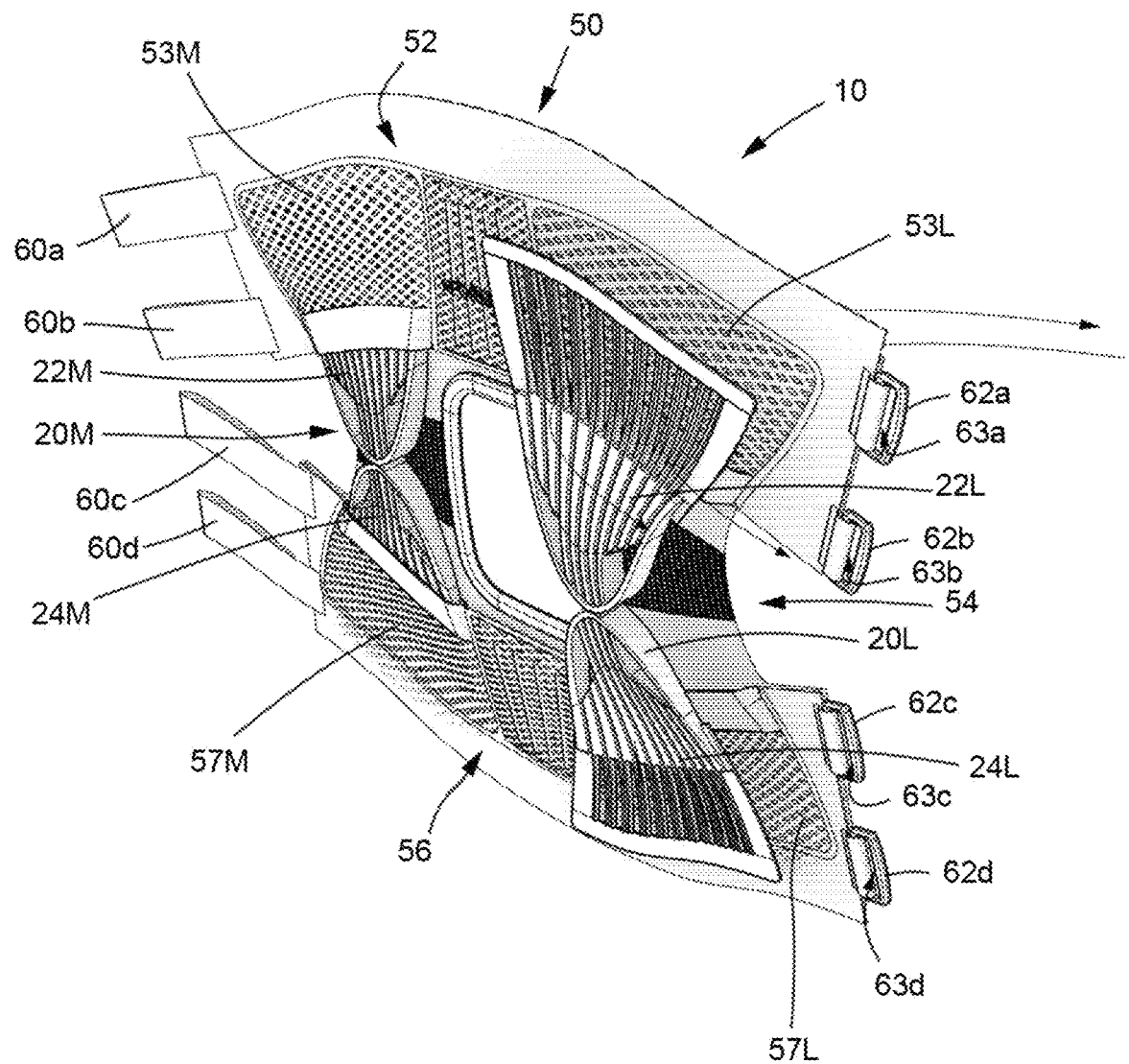
FIG. 13 is a top-left perspective view of a protective support of the present invention, shown in a partially assembled arrangement.
Figure 14:
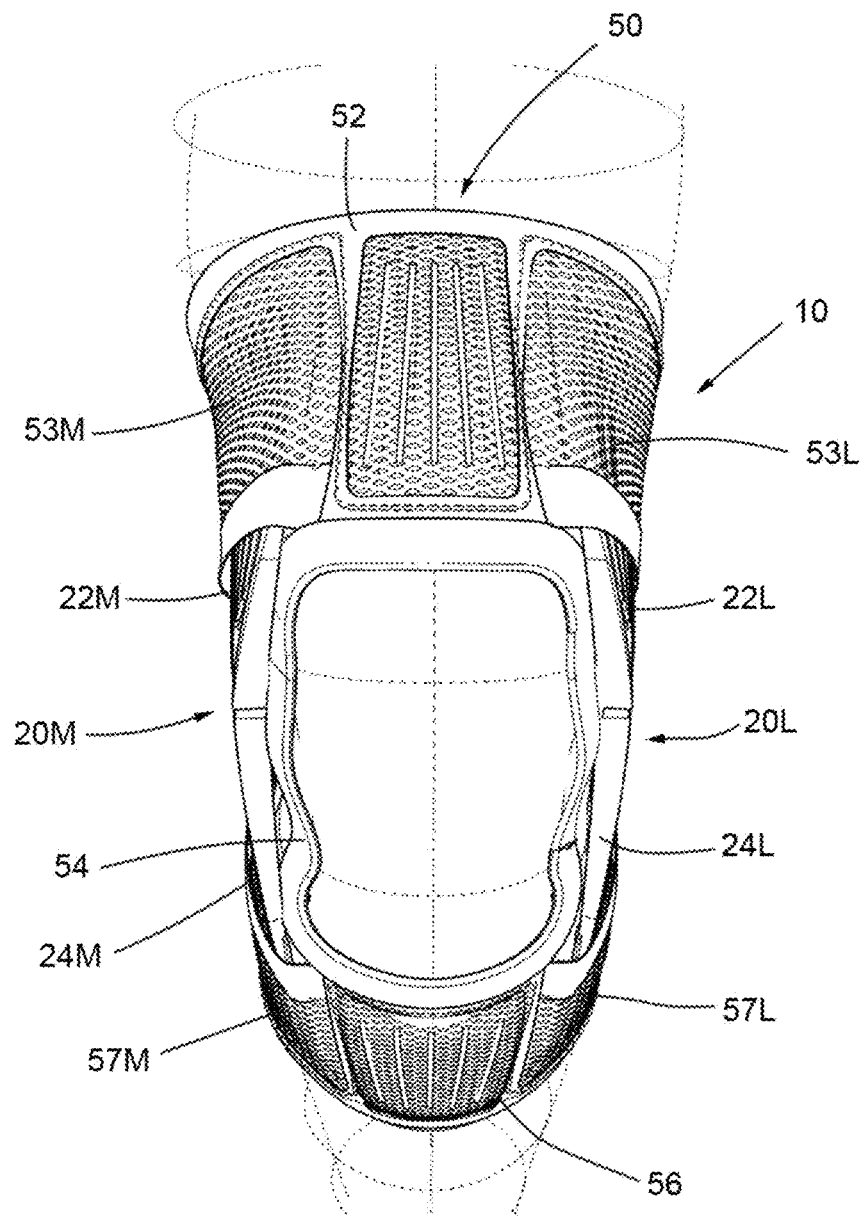
FIG. 14 is a perspective view of a protective support of the present invention, shown from the anterior of an individual's left knee.
Figure 15:
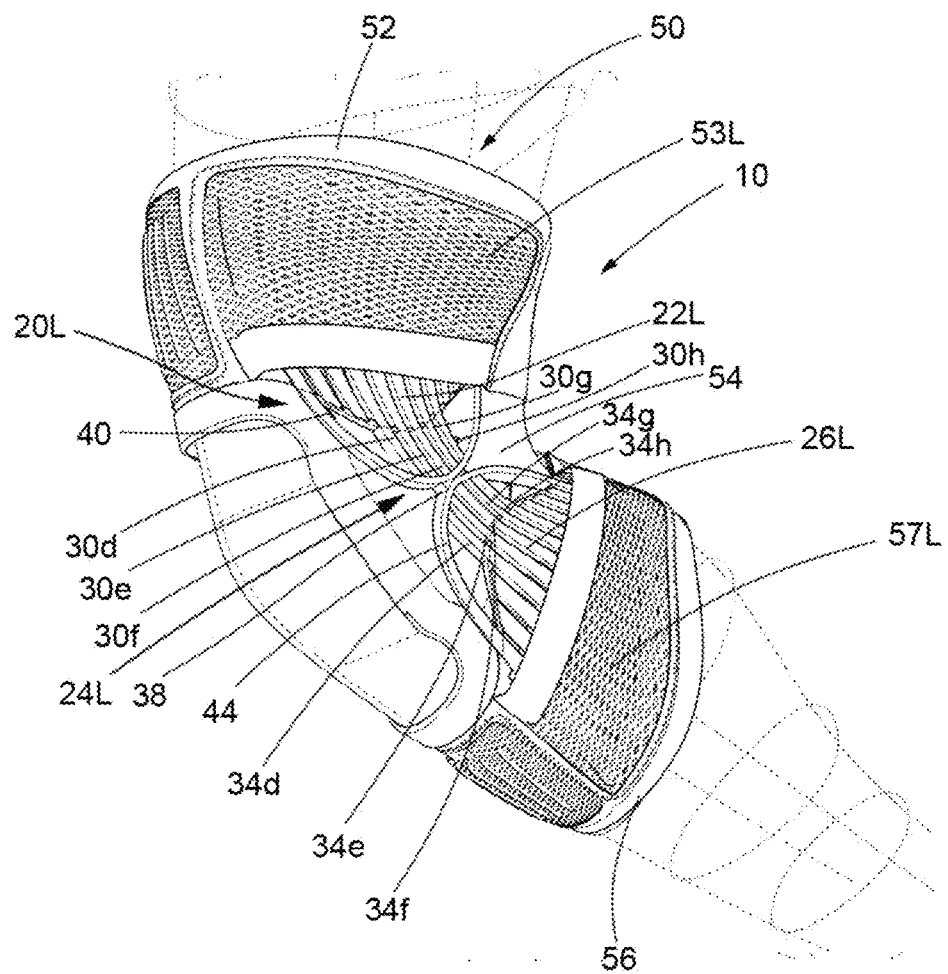
FIG. 15 is a perspective view of an alternate embodiment of the protective support present invention shown from the lateral side of an individual's left knee.

One preferred embodiment of support 10 is shown in a partially assembled arrangement in FIG. 13 and a fully assembled arrangement in FIGS. 14-15. In this embodiment, support structure 50 is adapted to cooperate with two hinges, 20M and 20L being disposed on the medial and lateral sides of the joint, respectively. In this embodiment, hinges 20M and 20L provide support for the affected joint or appendage. Support structure preferable comprises a superior section 52, an inferior section 56, and an intermediate section 54 therebetween. Superior section 52 defines a medial pocket 53M and a lateral pocket 53L, while inferior section 56 defines a medial pocket 57M and a lateral pocket 57L. Thus, medial pockets 53M, 57M are adapted to receive the superior section 22M and inferior section 24M, respectively, of medial hinge 20M, while lateral pockets 53L, 57L are adapted to receive the superior section 22L and inferior section 24L, respectively, of lateral hinge 20L (as shown in FIG. 13).

Structure 50 is preferably made from a comfortable material appropriate for contact with a joint or appendage that moves frequently, such a neoprene, spandex, or other similar materials that are commonly known and used in athletic supports an braces. Structure 50 may be perforated or provided with a series of apertures that improve airflow and moisture management for the affected joint. Pockets 53M, 53L, 57M, 57L are preferably formed from a lightweight, stretchable material, and may also have perforations to allow for airflow. A wearer may grasp and stretch open superior medial pocket 53M and insert the superior section 22M of hinge 20M therein. Once inserted, the wearer may release the pocket which will return to its original form and apply a compressive retaining force on hinge superior section 22M. The wearer may then repeat this process with inferior medial pocket 57M and hinge inferior section 24M, as well as with lateral pockets 53L, 57L and the superior and inferior sections 22L, 24L of lateral hinge 20L. Thus, it should be apparent that hinges 20M, 20L are removable from structure 50, and may be replaced with alternate hinges that, due to varying thickness or material properties, may provide greater stiffness or lateral support for immobilization or strength training, or are other desirable adaptations, such as perforated to allow for greater airflow during warmer seasons.

It should be appreciated that while preferably, it is not required that support 10 allow for removal and interchangeability of hinges. Instead, hinges that are attached to the support structure by any number or known permanent or semi-permanent means, such as stitches, zippers, brads, rivets, or high-strength adhesive are contemplated within the scope of this invention. Additionally, is should be appreciated that the hinges may be incorporated into a smaller bandage or splint sized appropriately for smaller joints, such as the metatarsophalangeal, proximal interphalangeal, or distal phalangeal joints of the fingers or toes.

In order to secure the support 10 to the individual's affected area and to adjust to the varying superficial dimensions of the individual's appendage at, for instance, the thigh and calf, superior and inferior sections 52, 56 are both equipped a plurality of adjustment straps 60a-d located in proximate to medial hinge 20M and a plurality of adjustment loops 62a-d located proximate to lateral hinge 20L. Each adjustment loop defines an internal aperture 63a-d. When worn, a free end of each adjustment strap 60a-d passes through an aperture 63a-d and doubles back upon itself. When formed from a material such as doubled-sided Velcro®, each strap 60a-d will adhere to itself thus securing the support 10 to the wearer's joint or appendage. Furthermore, the wearer can easily adjust the tension applied by the adjustment straps 60a-d by simply releasing the Velcro, adjusting the tension, and then re-adhering the strap to itself. In this embodiment, straps 60a-d and loops 62a-d are located such that straps are adjusted at the posterior of the joint, in this case, a knee. However, it should be appreciated that the straps may be positioned such that the adjustment occurs at the anterior of the joint. Likewise, the position of the straps and loops may be altered such that the straps 60a-d are located proximate to the lateral hinge 20L while loops 62a-d are located proximate to medial hinge 20M. Furthermore, to increase the grip and security of support 10 in areas that move frequently, silicon strips or dots or other similar structures may be provided on the interior of structure 50.

It should be appreciated that several variations of structure 50 may be substituted for the embodiment described immediately above. For instance, instead of straps and rings, structure 50 may utilize only straps be provided that are equipped with a plurality of Velcro® or similar hook structures which may be releasably attached to associated loop structures provided directly on the surface of structure 50. Alternatively, support structure may comprise one or more cylindrical sleeve(s) made of stretchable material such as neoprene or spandex. In this embodiment, the wearer would insert the affected appendage or joint into the sleeve or sleeves, thereby stretching the sleeve(s)'s material. The materials stretching action would then exert a compressive force upon the joint, thereby keeping the support structure in place. Alternatively, straps and buckles, or similar devices commonly used for quick adjustment may be substituted.

Referring now to FIG. 15, a preferred embodiment of support 10 is shown as worn by an athlete on the right knee viewed from the medial side in a flexed position. When worn on a knee or other hinge joint, such as an elbow, the design of hinges (only one of which, 20L, is visible in FIG. 15) provides therapeutic and rehabilitative benefits as well as reduced likelihood of injury. When support 10 is worn properly, the joint's movement during flexion exerts a moment on both superior section 22L and inferior section 26L. In response to the joint's flexion, longitudinal ribs 30d-h and 34d-h, transverse ribs 40 and 44, and intermediate rib 38 deflect and bend, creating an internal spring force within the hinge. This spring force is the result of the hinge's preferred resilient materials and graduated profile in which the hinge's profile thickness increases from the sections 22L, 26L to its greatest thickness in the vicinity intermediate section 24L, and in particular intermediate rib 38 (as discussed in connection with FIGS. 3 and 4 above). The internal spring force increases as the joint moves from an extended position to a flexed position. Thus, the increasing spring force prevents the joint from hyperflexion and common injuries associated therewith, such as damage or tears to the posterior cruciate ligament (PCL). The development of the spring force during flexion can also be used for strength training, as the wearer may repeatedly flex the joint to work against the building spring force, thereby strengthening the muscles proximate to the joint.

Figure 4A:
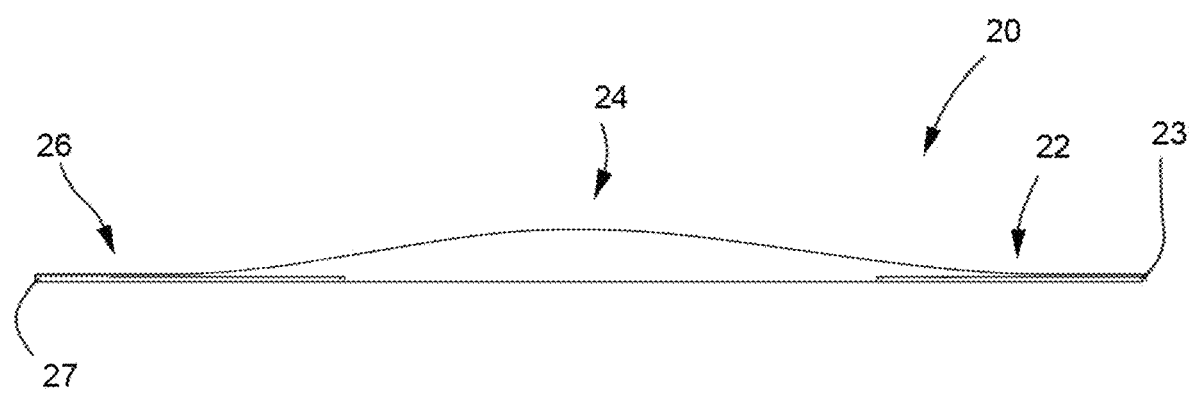
FIG. 4a a right-side elevation view of a hinge element of the present invention.

With reference now to FIGS. 4a-4b and FIGS. 5a-5b, the varying cross-sectional thickness of the hinge (described above, briefly) is more clearly visible. In particular, FIG. 4a provides a right-side elevation view of a preferred embodiment of the hinge, and demonstrates that hinge's graduated thickness preferably increases from its minimum in the vicinity of distal edges 23, 27 to its maximum the vicinity of intermediate section 24. While hinge joints such as the knee and elbow are adapted to allow for a limited degree of medial or lateral rotation, such rotation is limited by the joint's collateral ligaments. However, excessive torsional forces on the joint can result in over-rotation and damage to the collateral ligaments and other internal structures. Just as the design of the hinge preferably creates an increasing spring force under flexion that prevents excessive bending of the joint, it likewise creates increasing torsional spring force during rotation that helps prevent excessive twisting of the joint. Thus, the embodiment of the hinge shown in FIG. 4a has its maximum thickness in the area where the joint flexes or rotates, thereby preventing the joint from excessive twisting or lateral movement that can result in common injures associated there with, such as damage or tear to the bursa, meniscus, or anterior cruciate ligament (ACL).

Figure 4B:
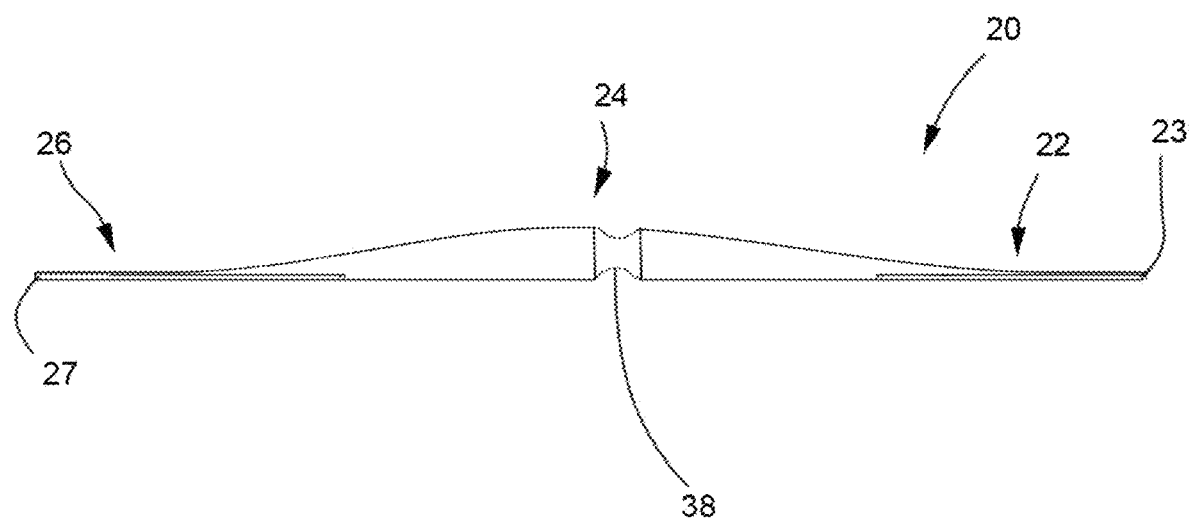
FIG. 4b a right-side elevation view of an alternate embodiment of a hinge element of the present invention.

FIG. 4b shows right-side elevation view an alternative embodiment where the cross-sectional thickness of hinge 20 likewise increases from its minum at the distal edges to a maximum near the intermediate section. However, in the embodiment shown in FIG. 4b the thickness of intermediate rib 38 decreases slightly. Such an arrangement may be preferable for athletes that require the hinge to provide greater bending support than torsional support or vice versa. Accordingly, the thickness of intermediate rib 38 may vary along the longitudinal length and/or transverse width of the hinge, and the specific dimensions may be determined based on the particular needs of the athlete or individual. In both embodiments shown in FIGS. 4a, 4b, the hinge provides the benefit of preventing injuries resulting from excessive bending or twisting of the joint.

In addition to providing increased or variable support in the intermediate section, relatively thin profile of the hinge in the vicinity of sections 22, 26 preferably remains flexible and allow the hinge to conform to the superficial contours of the individual's appendage or joint. Unlike hinges formed from metals or hard plastics which are largely immovable, the hinge of the present invention conforms to the appendage, even as differing muscle groups contract or relax. Because muscles can contract in multiple ways (for example, isometric contraction as opposed to isotonic contraction), such contractions can change the anatomical topography proximate to the muscles as they contract and relax. Thus, the flexibility and conformability of the hinge in sections 22, 26 creates a comfortable and more versatile hinge when compared with prior designs.

Finally, the graduated profile provides a final advantage in that it provides maximum protection against superficial wounds resulting from abrasion. The thicker profile in the intermediate section protects the joint while the thinner profile of the superior and inferior sections protects the skin.

Figure 16:
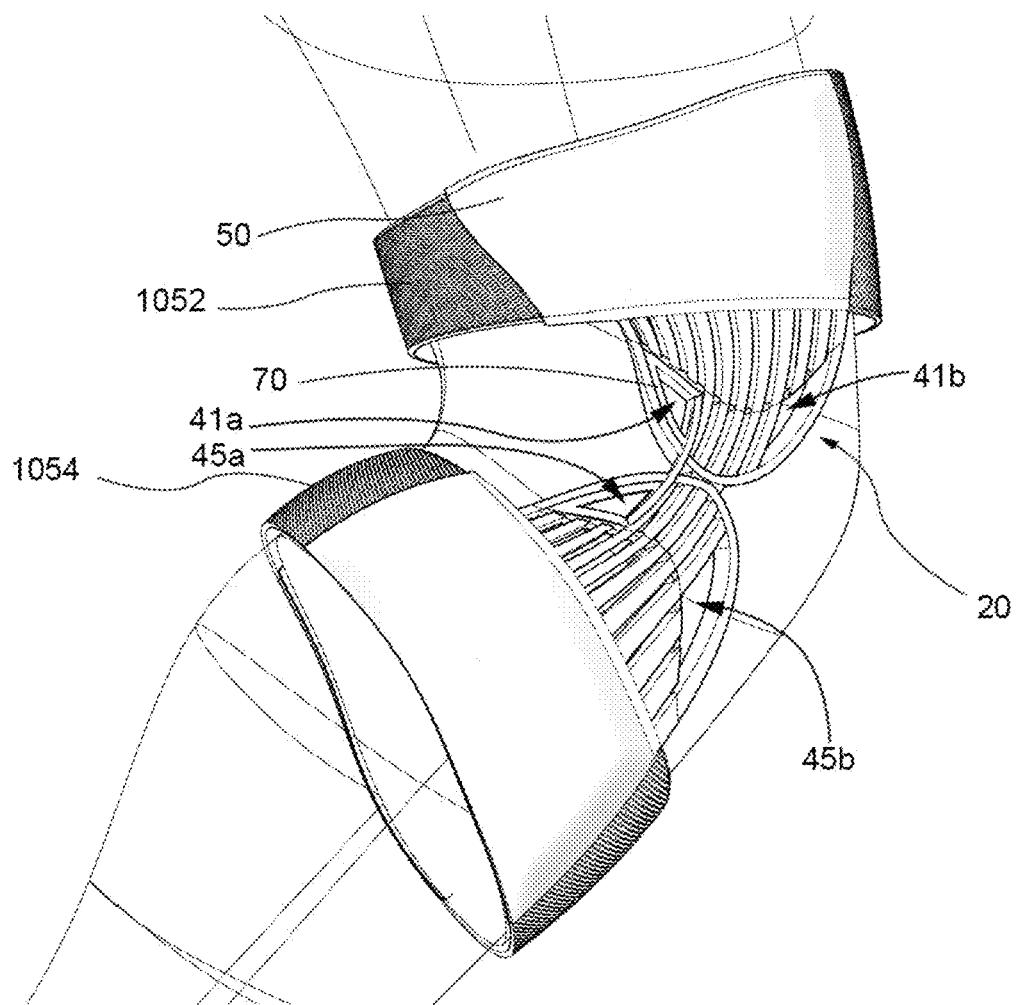
FIG. 16 is a perspective view of an alternate embodiment of the protective support present invention shown from the medial-posterior side of an individual's left knee.

Referring now to FIG. 16, hinge 20 is combined with an optional stiffening insert 70. Stiffening inserts may be optionally used with embodiments of hinge 20 that include superior adjustment recess 41a, 41b, and inferior adjustment recesses 45a and 45b (best visible in FIG. 2) Preferably formed from a durable elastomeric material such as TPU or EVA, the stiffening inserts are inserted into and releasably retained within adjustment recesses 41a, 41b, 45a and 45b as shown can increase the structural rigidity of the hinge, thereby offering increased protection for the joint. In this way, the wearer may quickly and easily adjust the level of support or protection available by inserting an insert with the desired stiffness.

Additionally, FIG. 16 shows an alternate version of support structure 50 where the adjustment straps and loops discussed above in connection with FIG. 13 are replaced with alternate structure in the form of compression bands 1052, 1054. In this embodiment, compression bands may be formed from neoprene, elastic band, or other resilient material suitable for comfortable compression fitting to human limbs.

Figure 17:
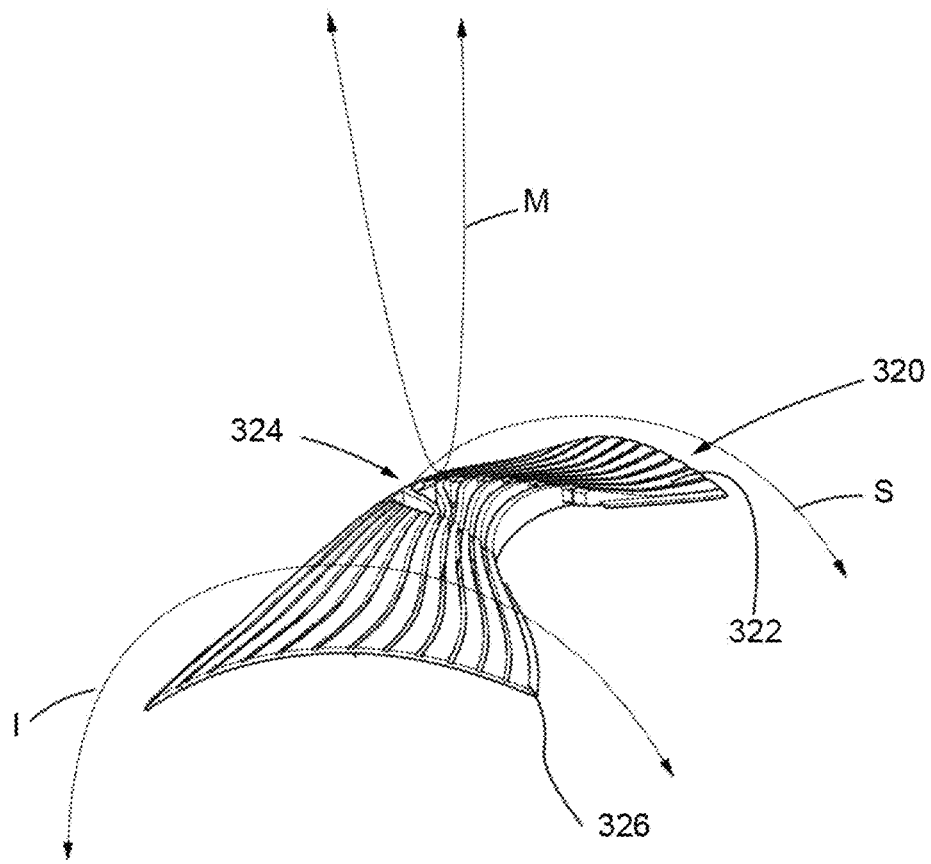
FIG. 17 is a perspective view of an alternate embodiment of a hinge element of the present invention.

FIG. 17 shows the versatility and utility of one embodiment of the hinge contemplated in the current invention, 320. The variable thickness describe in detail above is particularly useful because the hinge's reduced thickness in the vicinity of superior section 322 and interior section 326 are well adapted to conform to the variable circumferential contours of human limbs, as shown by contour arcs S and L. Additionally, the increased thickness of the hinge in the vicinity of intermediate section 324 is resistant to bending stresses along contour arc M. In this way, the hinge is both adapted to comfortably conform to human limbs and to provide support to hinge joints during flexion.

Although several embodiments have been shown and described by way of example, it should be appreciated by those skilled in the art that changes may be made to these embodiments without departing from the principles and spirit of invention, the scope of which is defined in the claims and their equivalents. For example, while certain operations have been described as being performed by a given element, those skilled in the art will appreciate that the operations may be divided between elements in various manners.

Although some example embodiments are described above with relation to muscular strength assisting apparatuses, those skilled in the art will appreciate that some example embodiments may be applied to other types of systems, such as systems not used in the field of medicine or athletic pursuits, such as industrial safety equipment and apparel, military protective devices and the like. Those skilled in the art will appreciate that the benefits of the invention disclosed herein may have a myriad of practical uses.

Although some example embodiments of the present disclosure have been shown and described, it should be appreciated by those skilled in the art that changes may be made in these example embodiments without departing from the principles and spirit of the invention, the scope of which is defined in the claims and their equivalents.

It should be understood that the example embodiments described herein should be considered in a descriptive sense only and not for purposes of limitation. Descriptions of features or aspects within each embodiment should typically be considered as available for other similar features or aspects in other embodiments.

I claim:

1. A protective support for spanning a joint in a body comprising:
   a. a support structure for securing said protective support to the body; and
   b. at least one elongated resilient hinge attached to said support structure and configured for spanning across a parasagittal plane of the joint, said at least one elongated resilient hinge having a length and a width, wherein said length is greater than said width, said at least one elongated resilient hinge further comprising:
   a first end adapted for releasable attachment to a portion of said support structure secured to the portion of the body superior to the joint;
   a second end adapted for releasable attachment to a portion of said support structure secured to the portion of the body superior to the joint; and
   an intermediate section therebetween;
   a plurality of resilient curvilinear longitudinal ribs that extend along said length of said at least one elongated resilient hinge from said first end to said second end; and
   at least one resilient curvilinear transverse rib extending along said width of said at least one elongated resilient hinge within said intermediate section and spanning said plurality of resilient curvilinear longitudinal ribs,
   wherein said at least one resilient curvilinear transverse rib and said plurality of resilient curvilinear longitudinal ribs together form a resilient array of support ribs within said intermediate section, and
   wherein an internal linear spring force develops within said intermediate section when said first end is bent towards said second end in response to flexion of the joint.

2. The protective support of claim 1, wherein said length and said width of said at least one elongated resilient hinge define an hourglass shape.

3. The protective support of claim 1, wherein said at least one elongated resilient hinge has a cross-sectional thickness that gradually increases along said length from said first end to said intermediate section and gradually decreases from said intermediate section to said second end.

4. The protective support of claim 1, wherein said support structure is a stretchable cylindrical sleeve.

5. The protective support of claim 1, wherein said support structure further comprises a first portion attached to said first end of said at least one elongated resilient hinge, and a second portion attached to said second end of said at least one elongated resilient hinge, and wherein said first portion and said second portion are independently adjustable to accommodate superficial contours of the joint and body.

6. The protective support of claim 5, wherein said support structure further comprises a plurality of adjustable straps for adjusting said first portion and said second portion to accommodate superficial contours of the joint.

7. The protective support of claim 1, wherein said at least one elongated resilient hinge is releasably attached to said support structure.

8. The protective support of claim 1, wherein said first end, said second end, and said intermediate section of said at least one elongated resilient hinge are formed as a single integral unit.

9. The protective support structure of claim 1, wherein a torsional spring force develops within said intermediate section when said first end is rotated in opposition to said second end in response to twisting of the joint.

10. A resilient hinge for a protective support for spanning a parasagittal plane of a joint in a body, said resilient hinge comprising:
 a. a superior end,
 b. an inferior end distal from said superior end, and
 c. an intermediate section disposed between said superior end and said inferior end;
 d. a plurality of resilient curvilinear longitudinal ribs that extend from said superior end to said inferior end, and
 e. at least one resilient curvilinear transverse rib extending along a width of said resilient hinge within said intermediate section and spanning said resilient curvilinear longitudinal ribs;
 wherein said at least one transverse rib and said longitudinal ribs together form a resilient array of support ribs in said intermediate section,
 wherein a torsional spring force develops within said resilient array of support ribs when said superior end is rotated in opposition to said inferior end in response to twisting of the joint, thereby preventing excessive twisting of the joint,
 said resilient hinge defining a length and a cross-sectional thickness, wherein said cross-sectional thickness gradually increases along-a said length from said superior end to said intermediate section and gradually decreases along said length from said intermediate section to said inferior end.

11. The resilient hinge of claim 10, wherein said superior end, said intermediate section, and said inferior end define an hourglass shape.

12. The resilient hinge of claim 10, wherein said cross-sectional thickness of said resilient hinge in said intermediate section prevents excessive bending and excessive rotation of the joint.

13. The resilient hinge of claim 10 wherein an internal linear spring force develops within said resilient array of support ribs when said superior end is bent towards said inferior end in response to flexion of the joint, thereby preventing hyperflexion of the joint, and.

14. The resilient hinge of claim 13, said hinge further comprising
 a. an anterior side,
 b. a posterior side, and
 wherein said at least one resilient curvilinear transverse rib extends from said anterior side to said posterior side across said plurality of resilient curvilinear longitudinal ribs.

15. The resilient hinge of claim 10, wherein said resilient hinge is attached to a support structure for securing said hinge to a said parasagittal plane of the joint.

16. The resilient hinge of claim 10, wherein said resilient hinge is releasably attached to a support structure.

17. A resilient hinge for a protective support for spanning a parasagittal plane of a joint in a body, said resilient hinge having an elongated shape that defines a length and a width, said resilient hinge further comprising:
 a. a superior end,
 b. an inferior end distal from said superior end,
 c. an intermediate section disposed between said superior end and said inferior end,
 d. at least one resilient curvilinear longitudinal rib extending along said length of said resilient hinge, and
 e. at least one resilient curvilinear transverse rib extending along said width of said hinge within said intermediate section and spanning said at least one resilient curvilinear longitudinal rib;
 wherein said at least one resilient curvilinear transverse rib and said at least one resilient curvilinear longitudinal rib together form a resilient array of support ribs adapted to flex in response to flexion of the joint,
 wherein said resilient hinge has a cross-sectional thickness that gradually increases along said length from said superior end to said intermediate section and gradually decreases along said length from said intermediate section to said inferior end,
 wherein said intermediate section develops an internal linear spring force therein when said superior end is bent towards said inferior end in response to flexion of the joint, thereby preventing hyperflexion of the joint; and
 wherein said intermediate section develops a torsional spring force therein when said superior end is rotated in opposition to said inferior end in response to twisting of the joint, thereby preventing excessive twisting of the joint.

18. The resilient hinge of claim 17 further comprising
 a. an anterior side,
 b. a posterior side, and
 wherein said at least one resilient curvilinear transverse rib extends from said anterior side to said posterior side across said at least one resilient curvilinear longitudinal rib.

19. The resilient hinge of claim 17, wherein said superior end, said intermediate section, and said inferior end together define an hourglass shape.

20. The resilient hinge of claim 17, wherein said resilient hinge is configured to be releasably attached to a support structure for securing said resilient hinge to a parasagittal plane of the joint.

* * * * *